United States Patent
Scholten et al.

(10) Patent No.: US 6,632,967 B2
(45) Date of Patent: Oct. 14, 2003

(54) PROCESS FOR THE PREPARATION OF UREA

(75) Inventors: Jacob F. Scholten, Maastricht (NL); Franciscus A. L. Van Laak, Geleen (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 10/126,951

(22) Filed: Apr. 22, 2002

(65) Prior Publication Data

US 2003/0135072 A1 Jul. 17, 2003

Related U.S. Application Data

(63) Continuation of application No. PCT/NL00/00702, filed on Oct. 1, 2000.

(30) Foreign Application Priority Data

Oct. 26, 1999 (NL) .............................................. 1013394

(51) Int. Cl.[7] ............................................. C07C 273/04
(52) U.S. Cl. ................................. 564/67; 68/69; 68/70; 68/71; 68/72
(58) Field of Search ............................... 564/67, 68, 69, 564/70, 71, 72

(56) References Cited

U.S. PATENT DOCUMENTS 3,940,440 A * 2/1976 Mavrovic ............... 260/555 A

FOREIGN PATENT DOCUMENTS

| JP | 10-182586 | 7/1998 |
| WO | 99 29663 | 6/1999 |

* cited by examiner

*Primary Examiner*—Peter O'Sullivan
(74) *Attorney, Agent, or Firm*—Pillsbury Winthrop LLP

(57) ABSTRACT

Process for the preparation of urea from ammonia and carbon dioxide in which the composition of the various process streams is measured via an ultrasonic measuring principle and in which the results of these measurements are used for process control. The process is particularly suitable for continuous measurements in a urea process.

17 Claims, 1 Drawing Sheet

PROCESS FOR THE PREPARATION OF UREA

This application is a continuation of International Application No. PCT/NL00/00702, filed Oct. 1, 2000, which designated the U.S.

The invention relates to a process for the preparation of urea from ammonia and carbon dioxide.

Urea can be prepared by introducing ammonia and carbon dioxide into a synthesis zone at a suitable pressure (for example 12–40 MPa) and a suitable temperature (for example 160–250° C.), which first results in the formation of ammonium carbamate according to the reaction:

Dehydration of the ammonium carbamate formed then results in the formation of urea according to the equilibrium reaction:

The theoretically attainable conversion of ammonia and carbon dioxide into urea is determined by the thermodynamic position of the equilibrium and depends on for example the $NH_3/CO_2$ ratio, the $H_2O/CO_2$ ratio and temperature, and can be calculated with the aid of the models described in for example Bull. of the Chem. Soc. of Japan 1972, Vol. 45, pages 1339–1345 and J. Applied Chem of the USSR (1981), Vol. 54, pages 1898–1901.

In the conversion of ammonia and carbon dioxide to urea there evolves as a reaction product a urea synthesis solution which consists essentially of urea, water, ammonium carbamate and unbound ammonia. In a urea process, the concentrations of the various components in this reaction product are determined and the measurement results are used for controlling the process. In particular the molar $NH_3/CO_2$ ratio (N/C ratio) is determined for controlling the $NH_3$ and/or the $CO_2$ feed to the synthesis. The N/C ratio is calculated as follows:

$$N/C = \frac{2 \text{ moles urea} + 1 \text{ mole } NH_3}{1 \text{ mole urea} + 1 \text{ mole } CO_2}$$

Besides the aforementioned urea synthesis solution, there may evolve in the synthesis zone a gas mixture of unconverted ammonia and carbon dioxide along with inert gases. Ammonia and carbon dioxide are removed from this gas mixture and are preferably returned to the synthesis zone. The synthesis zone may comprise separate zones for the formation of ammonium carbamate and urea. These zones may, however, also be united in a single apparatus.

The conversion of ammonium carbamate into urea and water in the reactor can be effected by ensuring a sufficiently long residence time for the reaction mixture in the reactor. The residence time will in general be longer than 10 min, preferably longer than 20 min. The residence time will in general be shorter than 2 hours, preferably shorter than 1 hour.

The conversion of ammonium carbamate into urea is an equilibrium reaction whose position is adversely effected by the water present in the reactor.

An important water source is the low-pressure carbamate stream which evolves during the further recovery of ammonia and carbon dioxide from the urea synthesis solution. This carbamate stream is rich in water and has an adverse effect on the conversion of ammonia and carbon dioxide into urea. This carbamate stream is, however, an important source of feedstocks, for which reason one chooses in most urea plants to return this carbamate stream to the synthesis zone all the same.

In practice, various processes are used for the preparation of urea. Initially, urea was prepared in so-called conventional high-pressure urea plants, which at the end of the 1960s were succeeded by processes carried out in so-called urea stripping plants.

A conventional high-pressure urea plant is understood to be a urea plant in which the decomposition of the unconverted ammonium carbamate into urea and the expulsion of the customary excess ammonia take place at a substantially lower pressure than the pressure in the synthesis reactor itself. In a conventional high-pressure urea plant the synthesis reactor is usually operated at a temperature of 180–250° C. and a pressure of 15–40 MPa. In a conventional high-pressure urea plant, following expansion, dissociation and condensation at a pressure of between 1.5 and 10 MPa, the reactants that are not converted into urea are returned to the urea synthesis as a carbamate stream. In addition, in a conventional high-pressure urea plant, ammonia and carbon dioxide are fed directly to the urea reactor. The N/C ratio in the urea synthesis in a conventional high-pressure urea process is between 3 and 5 and $CO_2$ conversion between 64 and 68%.

Initially, such conventional urea plants were designed as so-called 'Once-Through' processes. Here, non-converted ammonia was neutralised with acid (for example nitric acid) and converted into ammonia salts (for example ammonium nitrate). It did not take long until these conventional Once-Through urea processes were replaced with Conventional Recycle Processes, in which all non-converted ammonia and carbon dioxide are recycled to the urea reactor as carbamate streams. The water percentage of these carbamate streams is determined. The result of this measurement is used for controlling the process. It is essential here that the amount of water be controlled such that the carbamate streams are just above the crystallisation point. This is essential in order to limit as much as possible the adverse effect of the amount of water on the synthesis. In the recovery section, non-converted ammonia and carbon dioxide are removed from the urea synthesis solution obtained in the synthesis reactor, in which process a urea in water solution evolves. Next, this urea in water solution is converted into urea in the evaporation section by evaporating water at reduced pressure. The urea concentration of the feed to the evaporation is determined for optimum control of evaporation. Especially steam consumption can be optimised in this way.

A urea stripping plant is understood to be a urea plant in which the decomposition of the ammonium carbamate that is not converted into urea and the expulsion of the customary excess ammonia largely take place at a pressure that is essentially almost equal to the pressure in the synthesis reactor. This decomposition/expulsion takes place in a stripper with or without addition of a stripping agent. In a stripping process, carbon dioxide and/or ammonia may be used as stripping agent before these components are added to the reactor. Such stripping is effected in a stripper installed downstream of the synthesis reactor; in it, the urea synthesis solution coming from the urea reactor, which contains urea, ammonium carbamate and water as well as ammonia, is stripped with the stripping agent with addition of heat. It is also possible to use thermal stripping. Thermal stripping means that ammonium carbamate is decomposed and the ammonia and carbon dioxide present are removed from the urea solution exclusively by means of the supply of heat. Stripping may also be effected in two or more steps. In a known process (IDR process) a first, purely thermal stripping step is followed by a CO2 stripping step with addition of heat. The gas stream containing ammonia and carbon dioxide exiting from the stripper is returned to the reactor whether or not via a high-pressure carbamate condenser.

In a urea stripping plant the synthesis reactor is operated at a temperature of 160–240° C. and preferably at a temperature of 170–220° C. The pressure in the synthesis reactor is 12–21 MPa, preferably 12.5–19.5 MPa. The N/C ratio in the synthesis in a stripping plant is between 2.5 and 4 and $CO_2$ conversion between 58 and 65%. The synthesis can be carried out in one or two reactors. When use is made of two reactors, the first reactor, for example, can be operated using virtually fresh raw materials and the second using raw materials entirely or partly recycled, for example from the urea recovery.

A frequently used embodiment for the preparation of urea by a stripping process is the Stamicarbon $CO_2$ stripping process as described in European Chemical News, Urea Supplement, of Jan. 17, 1969, pages 17–20. The greater part of the gas mixture obtained in the stripping operation is condensed and adsorbed in a carbamate condenser, after which the high-pressure ammonium carbamate stream formed is returned to the synthesis zone for the formation of urea. The stripping of the urea synthesis solution with a stripping medium can take place in more than one stripper.

The high-pressure carbamate condenser may be designed as, for example, a so-called submerged condenser as described in NL-A-8400839. The submerged condenser can be placed in horizontal or vertical position. It is, however, particularly advantageous to carry out the condensation in a horizontal submerged condenser (a so-called pool condenser; see for example Nitrogen No 222, July-August 1996, pp. 29–31), because, in comparison with other designs of this condenser, the liquid generally has a longer residence time in the pool condenser. This results in the formation of extra urea, which raises the boiling point, so that the difference in temperature between the urea-containing carbamate solution and the cooling medium increases, resulting in better heat transfer.

After the stripping operation, the pressure of the stripped urea synthesis solution is reduced to a low level in the urea recovery after which urea is released and a low-pressure carbamate stream is recirculated to the synthesis section. Depending on the process, this carbamate may be recovered in either a single or a plurality of process steps operating at different pressures. In a stripping plant, too, the urea concentration in the feed stream to the evaporation and the water content of the low-pressure carbamate stream are measured, the results being used for process control.

In a urea plant, the compositions of the various streams are measured in various ways. The N/C ratio in the solution exiting from the synthesis reactor, for example, is measured with the aid of a commercially obtainable N/C meter (supplied by for example This Analytical B.V. in collaboration with Stamicarbon B.V.). JP-A-960341520 describes such an N/C meter. The water content of the low-pressure carbamate stream is measured by a commercially obtainable water meter. All these measurements are based on inter alia the density of the stream to be measured.

The drawback of all these measuring techniques is that the measurements take place outside the direct process. This invariably results in complex sampling techniques, in particular sampling in the high-pressure section of the urea plant or in the evaporation section operating at reduced pressure. As a consequence, all these measurements are difficult to conduct and so require costly equipment. Furthermore, these measurements are highly prone to failure.

The object of the invention is to provide a simple and cheap technique for conducting measurements in the various streams in a urea plant for the purpose of determining the compositions of the streams.

It has been found that the composition of the various streams in a urea plant can be determined via an ultrasonic measuring principle. According to this ultrasonic measuring principle the sound velocity in the liquid and/or gas stream is measured. It has been found that the sound velocity in a stream at a particular temperature, pressure and inert flow is a measure of the composition of that stream. The inert flow is the flow of the amount of air, supplied to the process together with one of the monomers, to protect the equipment against corrosion (passivation air).

According to this measuring principle, two or more sensors of the measuring instrument are placed on both sides of a stream to be measured, with one of the sensors emitting an acoustic signal and another sensor processing that signal.

By measuring the sound velocity in the streams in a urea plant by means of an ultrasonic measuring principle it is possible to determine the composition of the streams under process conditions. The measured speed of sound is indicative of the composition.

Various suitable embodiments of the ultrasonic meter are possible.

In a first embodiment use is made of a meter mounted onto a pipeline (clamp-on meter). In the case of this meter, the sensors are mounted outside of the pipeline. The flow rate and the sound velocity are measured by way of measurement signal. The advantage of this technique is that the sensors do not come into contact with the process fluid. A disadvantage might be that, if the medium has two physical states, there does exist the possibility of gas bubbles, which may absorb and scatter the emitted signal, which may lead to reduced reliability of the meter. It may be said, however, that where a meter is mounted onto a line, the measurement is suitable for brief measurements in processes in which no or only few gas bubbles are present. In a urea plant, this embodiment is for example suitable for measuring the amount of water present in the urea being passed to the evaporation with the measured values being used to control and optimise steam consumption.

In a second embodiment use is made of a so-called in-line meter. In this case the sensors are mounted in the pipe wall. This meter produces the same measurement signals as the clamp-on meter. Also, this meter permits a so-called multi-beam to be configured by adding sensors. When a sensor pair fails because of malfunction of a sensor or because too many gas bubbles are crossing the acoustic path of that sensor pair, then a suitable measurement is still available. An advantage is that this meter is especially suitable for deployment as a continuous measurement. This in-line embodiment is for example suitable for measuring the N/C ratio in the urea synthesis solution leaving the urea reactor. This N/C measurement is used for control of the ammonia and/or carbon dioxide flow to the synthesis section.

In a third embodiment an insertion meter is inserted in the line through a nozzle. From an instrument engineering viewpoint, deployment of this embodiment may be considered when gas bubbles interfere with the in-line meter such that no reliable measurement is obtained. The insertion meter measures over a substantially shorter distance, which may imply that the number of bubbles that may interfere with the measurement is smaller and also that the emitted energy travels a shorter distance, which by definition leads to a stronger sensor signal. Accordingly, a major advantage is that this meter is the least affected by gas bubbles. Also, this meter is suitable for continuous service. This embodiment is for example suitable for measuring the N/C ratio of the ammonia containing carbamate stream from the high-pressure carbamate condenser to the reactor. In a urea plant employing a separate high-pressure carbamate condenser, this N/C meter allows the reactor to be controlled more quickly and more accurately.

The advantages of this ultrasonic measuring technique in a urea plant include the following:
  no complex sampling is necessary
  no sample conditioning is necessary
  higher availability than known equipment
  higher reliability than known equipment
  lower investment costs than in the case of known equipment
  lower maintenance costs In consequence, the invention also relates to a process for preparing urea from ammonia and carbon dioxide in which the composition of the various process streams is measured via an ultrasonic measuring principle and in which the results of such measurements are used for controlling the process.

The invention is especially suitable for determining the N/C ratio in the liquid stream leaving the urea reactor. The ammonia and/or carbon dioxide feed to the synthesis is optimised with the aid of the results of these measurements.

It has also been found that the invention is highly suitable for determining the water content of the low-pressure carbamate stream. The amount of water passing in this stream to the synthesis is minimised using the results of these measurements.

The invention has also been found to be highly suited for measuring the composition of the carbamate stream which in a urea stripping plant evolves in the high-pressure carbamate condenser and is passed to the urea-reactor along with ammonia. More particularly, the invention has been found to be especially suitable for measuring the composition of the carbamate stream which in a urea stripping plant evolves in the horizontally positioned submerged carbamate condenser and which is passed to the synthesis along with ammonia. The feedstock streams to the synthesis are controlled with the results of these measurements.

The invention is also advantageous for conducting measurements in a urea plant. In a urea plant the capacity measurement according to the invention can take place downstream of the dissociation and upstream of the intermediate storage which contains the urea solution being passed to the evaporation. The advantage of measuring the product stream at this point is that the plant's nitrogen balance is complete at this point, which is an important element in calculating the strippet efficiency and also the steam consumption per ton urea. Also, by conducting measurements here, better control (feed forward control) of the low-pressure section of the urea plant is possible.

Furthermore, the invention is highly suited for improving and optimising existing urea plants.

The invention can be used in all current urea processes, both conventional urea processes and urea striping processes. Examples of conventional urea processes in which the invention can be used are the so-called Once-Through, Conventional Recycling and Heat Recycling Processes. Examples of urea stripping processes in which the invention can be used are the $CO_2$ stripping process, the ammonia stripping process, the self-stripping process, the ACES process (Advanced process for Cost and Energy Saving), the IDR (Isobaric-Double-Recycle) process and the HEC process.

Also in a process described in US-A-5767313 the method according to the present invention can be used. In this socalled poolreactor process the N/C measurement can be executed inside or outside the reactor.

The invention relates in particular to a process for the preparation of urea from ammonia and carbon dioxide in which:

$NH_3$ and $CO_2$ are supplied to the high-pressure section of a urea plant and are converted in a reactor into a liquid stream (1) consisting essentially of urea, ammonium carbamate, water and ammonia and a gas stream (2) consisting essentially of ammonia, carbon dioxide, water vapour and inert gases;

this liquid stream (1) is separated into a gas stream (3) consisting essentially of ammonia, carbon dioxide and water vapour and a liquid stream (4) consisting essentially of urea and water;

this liquid stream (4), following expansion, is passed to a reduced-pressure section where there are obtained one or more gas streams (5) consisting essentially of ammonia, carbon dioxide and water vapour and liquid stream (6) consisting essentially of urea and water;

this liquid stream (6)(optionally via intermediate storage as liquid stream (7)) is passed to an evaporation section where virtually water-free urea is released;

the various gas streams (5) are condensed and recirculated as low-pressure carbamate solution (8) to the synthesis section, where it absorbs gas stream (2), and is passed to the high-pressure carbamate condenser as carbamate stream (9);

the gas stream (3) is condensed with the aid of carbamate stream (9) in the high-pressure carbamate condenser, in which process carbamate stream (10) evolves, which is passed to the synthesis, and in which process the composition of the various streams is determined via an ultrasonic measuring principle and in which the urea process is controlled with the result of the

Figure 1:
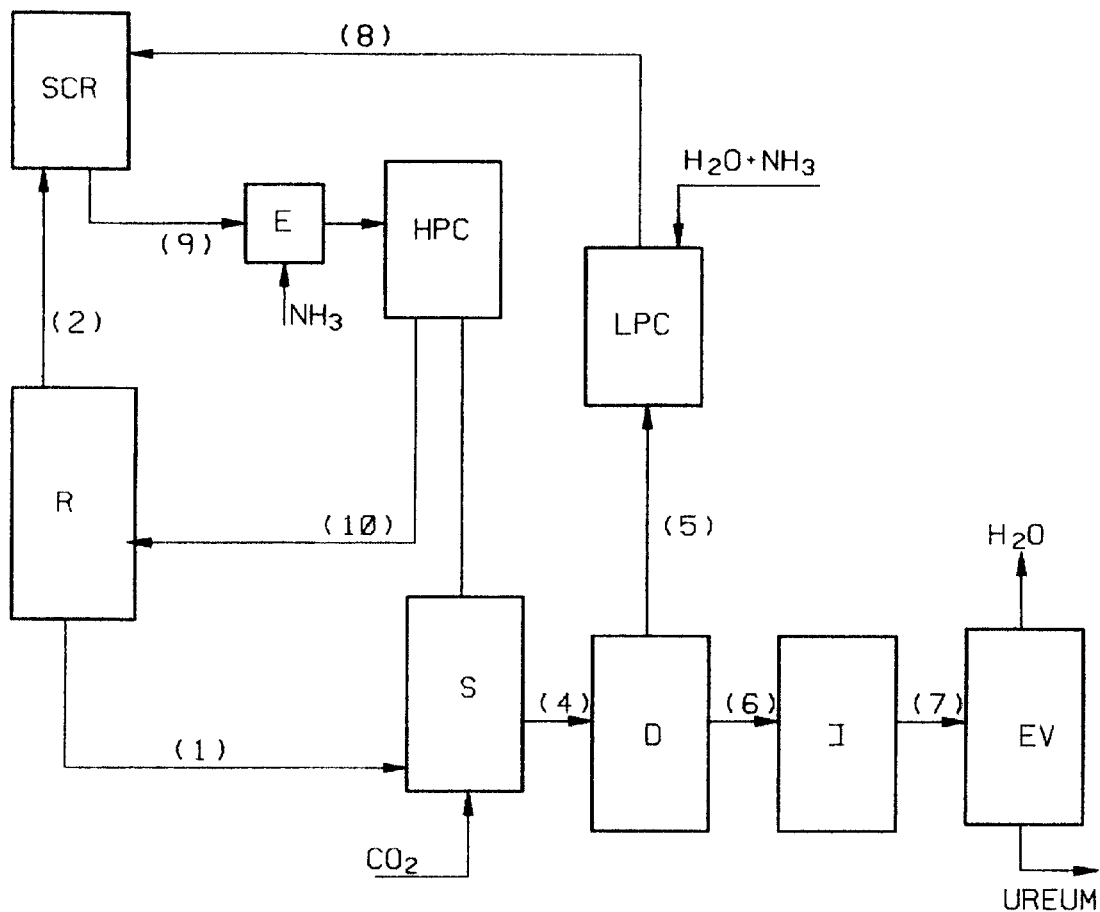
FIG. 1 shows by way of example a schematic representation of an embodiment of the invention for the Stamicarbon $CO_2$ stripping process. In the reactor(R), at a temperature of between 170 and 220° C. and at a pressure of between 12.5 and 19.5 MPa, ammonia and carbon dioxide are converted into a urea synthesis solution (1) consisting essentially of urea, ammonium carbamate, water and ammonia. In the process there is also obtained a gas stream (2) consisting essentially of ammonia, water vapour, carbon dioxide and inert gases. In scrubber (SCR) the ammonia, water vapour and carbon dioxide are transferred herefrom to the low-pressure carbamate stream (8) coming from the recovery. The urea synthesis solution (1) is passed to stripper (S) where the urea synthesis solution is stripped with the carbon dioxide required for the process. The stripped gases leave the stripper as stream (3) which stream consists essentially of ammonia, carbon dioxides and water vapour. Following expansion, the stripped urea synthesis solution (4) is fed to the dissociation (D) where the remaining ammonium carbamate is converted to ammonia and carbon dioxide, which along with the free ammonia and carbon dioxide present in the solution (4) coming from the stripper, are discharged from the dissociation as gas stream (5). The urea solution (6)

evolving in the dissociation, consisting essentially of water and urea, passes to an intermediate storage (I). The urea solution (7) is passed from this intermediate storage (I) to the evaporation (EV) where the water is removed from the solution and virtually water-free urea is obtained. Gas stream (5), consisting essentially of ammonia, carbon dioxide and water vapour, is condensed and converted to a low-pressure carbamate solution in a condenser (LPC) which operates at low pressure. This low-pressure carbamate solution (8) is passed to scrubber (SCR) to scrub ammonia, carbon dioxide and water vapour out of the vapour stream (2) exiting the reactor. With the aid of an ammonia ejector (E) a carbamate stream (9) is passed from scrubber (SCR) to the high-pressure condenser (HPC) to cause gas stream (3) from stripper (S) to condense. A concentrated carbamate stream (10) is passed from the high-pressure carbamate condenser to the urea synthesis. In the streams (1), (6), (8) and (10) there are placed sensors on or in the lines through which these gas streams and/or liquid streams are transported for measuring the sound velocity and, by derivation, the composition.

The sound velocity and thus the composition in the stream can be determined in the different locations using different embodiments. The N/C ratio in the urea synthesis solution (1), for example, is preferably measured with the in-line meter although the insertion meter gives good performance here too. Production immediately downstream of the dissociation (D) in stream (6) or (7) are for example measured with an in-line meter although a line-mounted meter also gives the correct compositions. The composition of the two carbamate streams (8) and (10) is for example measured via an insertion meter although an in-line meter is well possible here too.

The following example further describes the present invention.

EXAMPLE I

In a urea with a capacity of 1100 ton/day, the sound velocity in the urea synthesis solution (point (1) in FIG. 1) was measured with a clamp-on meter. The pressure in the reactor was 14.2 Mpa, the temperature 182° C. and the inert flow into the reactor was 950 kg air/hour. The sound velocity was measured 42 times. The average value was 1990 m/sec. The standard deviation was 2.2 m/sec. The N/C value was 2.85 and was determined with the aid of a calibraction graph.

What is claimed is:

1. Process for the preparation of urea from ammonia and carbon dioxide, characterised in that the composition of the various process streams is measured via an ultrasonic measuring principle, with the results of these measurements being used for process control.

2. Process according to claim 1, characterized in that the N/C ratio in the liquid stream exiting from the synthesis is determined.

3. Process according to claim 1, characterized in that the water content in the low-pressure carbamate stream is determined.

4. Process according to claim 1, characterized in that the urea content in the feed stream to the urea evaporation is determined.

5. Process according to claim 1, characterized in that there is determined the composition of the carbamate stream evolving in the high-pressure carbamate condenser a urea stripping plant, which stream is passed to the synthesis along with the ammonia.

6. Process according to claim 5, characterized in that there is determined the composition of the carbamate stream evolving in the horizontal submerged carbamate condenser in a urea stripping plant, which stream is passed to the synthesis along with the ammonia.

7. Process for the preparation of urea from ammonia and carbon dioxide in which:
   NH3 and $CO_2$ are supplied to the high-pressure section of a urea plant and are converted in a reactor into a liquid stream (1) consisting essentially of urea, ammonium carbamate, water and ammonia and a gas stream (2) consisting essentially of ammonia, carbon dioxide, water vapour and inert gases;
   this liquid stream (1) is separated into a gas stream (3) consisting essentially of ammonia, carbon dioxide and water vapour and a liquid stream (4) consisting essentially of urea and water;
   this liquid stream (4), following expansion, is passed to a reduced-pressure section where there are obtained one or more gas streams (5) consisting essentially of ammonia, carbon dioxide and water vapour and liquid stream (6) consisting essentially of urea and water;
   this liquid stream (6) is passed to an evaporation section where virtually water-free urea is released;
   the various gas streams (5) are condensed and recirculated as low-pressure carbamate solution (8) to the synthesis section, where it absorbs gas stream (2), and is passed to the high-pressure carbamate condenser as carbamate stream (9);
   the gas stream (3) is condensed with the aid of carbamate stream (9) in the high-pressure carbamate condenser, in which process carbamate stream (10) evolves, which is passed to the synthesis, characterized in that the composition of the various streams is determined via an ultrasonic measuring principle and in which the urea process is controlled with the results of the measurements.

8. Process for improving and optimising existing urea plants by application of claim 1.

9. Process according to claim 1, wherein the step of measuring composition via an ultrasonic measuring principle comprises measuring sound velocity of a said process stream via sensors which are not in contact with the process stream.

10. Process according to claim 1, wherein said process stream whose composition is measured via said non-contacting sensors, comprises the water-containing urea-feed stream to the urea evaporation.

11. Process according to claim 1, wherein the measured sound velocity is used to determine water content of the water-containing urea-feed stream, said process further comprising using the water content information to control and optimize steam consumption.

12. Process according to claim 1, wherein the step of measuring composition via an ultrasonic measuring principle comprises measuring sound velocity of a said process stream via at least one pair of sensors mounted in contact with the process stream.

13. Process according to claim 12, wherein said process stream whose composition is measured via said contacting sensors, comprises the urea synthesis solution leaving the urea reactor.

14. Process according to claim 13, wherein the measured sound velocity is used to determine nitrogen/carbon (N/C) ratio of the urea synthesis solution, said process further comprising using the N/C ratio for controlling ammonia and/or carbon dioxide flow to the synthesis section.

15. Process according to claim 1, wherein the step of measuring composition via an ultrasonic measuring principle comprises measuring sound velocity of a said process stream via an insertion meter inserted into said process stream through a nozzle.

16. Process according to claim 15, wherein said process stream whose composition is measured via said insertion meter is the ammonia-containing carbamate stream from the high-pressure carbamate condenser to the reactor.

17. Process according to claim 16, wherein the measured sound velocity is used to determine nitrogen/carbon (N/C) ratio of the said carbamate stream is measured, said process further comprising using the N/C ratio for controlling the reactor.

* * * * *